(12) United States Patent
Hardcastle (10) Patent No.: US 7,417,728 B2
(45) Date of Patent: Aug. 26, 2008

(54) FULL SPECTRUM MONITORING FOR OUTDOOR ACCELERATED WEATHERING DEVICE

(75) Inventor: Henry K. Hardcastle, Phoenix, AZ (US)

(73) Assignee: Atlas Material Testing Technology LLC, Chicago, IL (US)

( * ) Notice: Subject to any disclaimer, the term of this patent is extended or adjusted under 35 U.S.C. 154(b) by 281 days.

(21) Appl. No.: 11/422,951

(22) Filed: Jun. 8, 2006

(65) Prior Publication Data
US 2007/0285654 A1 Dec. 13, 2007

(51) Int. Cl.
G01J 3/00 (2006.01)
(52) U.S. Cl. .................... 356/300; 73/865.6
(58) Field of Classification Search ........... 356/300; 73/865.6
See application file for complete search history.

(56) References Cited

U.S. PATENT DOCUMENTS

| | | | |
|---|---|---|---|
| 4,391,522 A | * | 7/1983 | Schmid et al. .............. 356/326 |
| 4,644,166 A | | 2/1987 | Sturm et al. |
| 5,136,886 A | | 8/1992 | Neigoff et al. |
| 5,206,518 A | | 4/1993 | Fedor et al. |
| 5,220,840 A | | 6/1993 | Neigoff et al. |
| 5,854,433 A | | 12/1998 | Patel et al. |
| 6,626,052 B1 | | 9/2003 | Martin et al. |
| 6,720,562 B2 | | 4/2004 | Rathod et al. |

* cited by examiner

Primary Examiner—F. L Evans
(74) Attorney, Agent, or Firm—Vedder Price P.C.

(57) ABSTRACT

Methods for directly comparing the light spectral power distribution of a natural light source to the light spectral power distribution received on the target area of an outdoor accelerated weathering device, comparing the spectral measuring assembly on accelerated weathering devices with traceable spectral measuring assemblies measuring the same light source at the same instant in time, comparing different outdoor accelerated weathering devices to one another with respect to continuous direct measurement of each such device in a collection relating the quality of each single device back to a single standard measured by all devices and rationalizing the results of different methods of weatherability testing.

36 Claims, 5 Drawing Sheets

FULL SPECTRUM MONITORING FOR OUTDOOR ACCELERATED WEATHERING DEVICE

BACKGROUND OF THE DISCLOSURE

The present disclosure is generally related to use of a spectral measuring device in connection with an outdoor accelerated weathering device, and more particularly, to methods for directly comparing the light spectral power distribution of a natural light source (the sun) to the light spectral power distribution received on the target area of an outdoor accelerated weathering device, comparing the spectral sensor on accelerated weathering devices with traceable sensors measuring the same light source (the sun) at the same instant in time, comparing different outdoor accelerated weathering devices to one another with respect to continuous direct measurement of each such device in a collection relating the quality of each single device back to a single standard measured by all devices and using a single spectrum measurement device design to rationalize the results of different methods of weatherability testing.

Conventional radiation measurements for outdoor weathering testing exposures are described in the appropriate primary standards: (1) ASTM G 90 describes the current method for outdoor accelerated weathering devices; and (2) ASTM G 7 describes the current method for outdoor real time weathering tests. Numerous other testing standard methodologies are known to those of skill in the art for specific applications and to attempt to list all such standards is unnecessary. In general, each conventional method uses broadband total solar and ultraviolet region measurement in calculations to determine the broadband solar radiant exposure of test specimens. These methods do not allow specific spectral wavelengths to be monitored for outdoor accelerated tests. These methods also do not allow measurement of radiant exposure of individual machines or a traceable method to determine the radiant exposure or spectral dose on individual outdoor accelerated weathering devices.

There are prior art references that disclose spectral monitoring devices. However, none of such references disclose methods for directly comparing indoor, outdoor real-time and outdoor accelerated methods. Nor do such references disclose calibration techniques or comparison of natural sunlight to concentrated natural sun light using the spectral monitoring devices of such references.

Generally, a variety of conventional methods have been used to determine radiant exposure (light dose) of specimens on natural end use non-accelerated exposures, namely: days, months and years by calendar; sunlight hours using focusing lenses and burned strips of paper; pyranometer devices measuring total solar radiation; and total ultraviolet radiometers ("TUVR") devices measuring ultraviolet wavebands. Additionally, a variety of conventional methods have been used to determine radiant exposure in artificial weathering chambers; namely: time, broadband wavelength filtered detectors; devices, such as broadband and narrowband photodetectors and radiometers; and dose calculations based on radiation flux integrated overtime.

Still further, a few conventional methods have been used to determine radiant exposure in outdoor accelerated (concentrated) weathering methods, namely: radiometers mounted remote to the accelerated weathering devices; comparison of shaded disc radiometers to radiometers not shaded; radiometers fitted with collimating tubes; and calculations based on assumed reflectance values of concentrating elements.

Calibration methods used to calibrate solar radiation sensors for use in outdoor accelerated weathering methods and outdoor real-time weathering tests use a multi-step calibration method to link radiation measurements back to a primary reference standard. This calibration chain is incomplete with respect to tests performed in outdoor accelerated weathering methods such as the fresnel-reflecting solar concentration devices.

The conventional method of calibration is generally summarized as follows: a primary reference sensor at the exposure laboratory is calibrated to a traceable light source in the laboratory, which is a standard from any suitable standards organization, such as may be available from National Institute of Standards and Technology. For example, a spectrophotometer measures a standard light source and the signal at each of the wavelengths measured by the spectrophotometer is adjusted to match the standard specified values for that light source. This primary reference sensor is then used side by side with other master standard measurement devices to measure the sun at the same moment in time. For example, a standard-traceable spectrophotometer is set up outside, under the sun next to master standard TUVRs, such as Model TUVR from The Eppley Laboratory Inc. of Newport, R.I. Both the spectrophotometer and TUVR devices measure the sun at the same moment and the TUVRs are adjusted until they measure the same as the standard-traceable spectrophotometer primary sensor. Note that a spectrophotometer is a spectral instrument that measures light at discreet wavelengths but that the TUVR is a total ultraviolet instrument and measures all light between 295 nm and 385 nm wavelengths. Simple calculations allow spectral data to be integrated to total ultraviolet data.

The master standard TUVR instruments are subsequently mounted side-by-side with working TUVR instruments to measure the sun at the same moment and the working TUVRs are adjusted to read the same values as the master TUVRs.

Two calibrated working TUVRs are then mounted on a tracking mount that follows the sun's movements in a similar manner as conventional outdoor accelerated weathering devices—one under a shading disc and the other direct to the sun—and measurements are taken in accordance with ASTM G 90 to calculate the discreet component of solar flux reaching the laboratory and the accelerated weathering devices therein.

The conventional method of using an average mirror reflectance of the entire field collection of outdoor accelerated weathering devices (i.e., the average reflectance of the entire field collection of outdoor accelerated weathering devices multiplied by the number of mirrors on each device) generates a single average calculated dose over a broad wavelength region that is determined for all materials on exposure regardless of which individual machine characteristics those materials were exposed under. For a more thorough discussion refer to ASTM G 90, which is hereby incorporated by reference herein.

Conventional methods do not directly measure concentrated sunlight on outdoor accelerated weathering machines and do not directly compare actual sunlight to concentrated sunlight on outdoor accelerated weathering machines. Conventional methods also introduce error due to the broadband measurements that were taken of the source of sunlight and then inferred through calculation to be what was deposited after concentration on the outdoor accelerated weathering device target boards. In fact, the mirror spectral reflectance may have changed its specific reflectance characteristics, which would not have been observed by remotely located broadband detectors. The spectral changes would have gone unaccounted for in conventional methods.

Conventional methods also use reflective factors from single narrow wavelength reflectance measurements of reflective elements installed on the outdoor accelerated weathering devices. The narrow waveband reflectance measurements do not accurately describe the actual spectral reflectance of the reflective elements and can cause considerable errors in calculating the concentration factor of individual outdoor accelerating weathering devices.

In conventional methods, the accumulated radiant exposure is not measured by individual systems mounted on individual machines, rather it is measured by a common system and applied to a collection of unique machines ignoring machine-to-machine variations. Moreover, conventional methods are based on a mirror reflectance value on the fresnel-reflecting concentrating devices. This is typically an average value obtained by averaging measurements from many different individual machines and mirror elements within each machine. The actual individual values for specific machines vary greatly from the average.

Conventional methods also do not take into account characteristics of individual machines. For instance, the mirror alignment (accurate alignment of reflected light beams in the target area) differ in quality from machine to machine. These individual machine differences are not accounted for in conventional methods. By actually measuring the solar spectral power distribution on the target board of individual machines using the unique methods disclosed herein, a more accurate measurement of actual light flux and radiant exposure can be obtained.

Conventional methods to correlate results obtained on different outdoor accelerated weathering devices, use broadband total solar and ultraviolet region measurement in calculations to determine the solar radiant exposure of test specimens. These methods do not allow specific spectral wavelengths to be monitored for the test. Further, conventional methods do not replicate the measurements obtained in the xenon arc chamber tests on tests performed in outdoor natural real-time exposures or outdoor accelerated exposure tests. The unique methods disclosed herein repeat the same measurements using the same devices in all three exposure types. By using the same device designs, more comparable simulations can be made and results from the three different weathering test methods are more comparable than the results obtained from conventional methods. It is important to note that conventional outdoor accelerated methods use a broad spectral region and not spectral wavelengths unique to different individual materials Therefore, there exists a need in the art for unique methods that allow true direct comparison of natural sunlight to concentrated sunlight in the target area of outdoor accelerated weathering devices, a more direct traceable path due to fewer steps in the calibration sequence for light monitors, all outdoor weathering devices in a field to be measured simultaneously using the same light source and correlation of weathering test results regardless of the type of weathering device used, that overcome the disadvantages described above, but also decrease cost and provide improved performance in use.

BRIEF DESCRIPTION OF THE DRAWINGS

Certain embodiments are shown in the drawings. However, it is understood that the present disclosure is not limited to the arrangements and instrumentality shown in the attached drawings, wherein.

DETAILED DESCRIPTION OF THE DISCLOSURE

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

In one aspect of the present disclosure, the method for determining a concentration factor for an outdoor accelerated weathering device includes a number of steps. Namely, orienting a first light collection device on a target board of the outdoor accelerated weathering device or exposure to concentrated sunlight. Next, orienting a second light collection device on an upper surface of the outdoor accelerated weathering device for exposure to direct sunlight, wherein the first and second light collection devices are substantially identical. Next, channeling the concentrated sunlight from the first light collection device and the direct sunlight from the second light collection device to a switch. Next, activating the switch between a first operative position and a second operative position such that one, of (a) the concentrated sunlight from the first light collection device and (b) the direct sunlight from the second light collection device, is directed to a common sampling structure in the first operative position and an other of (x) the concentrated sunlight from the first light collection device and (y) the direct sunlight from the second light collection device, is directed to the common sampling structure in the second operative position. Next, orienting a spectral measuring device to observe the concentrated sunlight and direct sunlight on the common sampling structure as a switch is activated between the first and second operative positions. Next, recording a first solar spectral power distribution from the common sampling structure when the switch is in the first operative position. Next, recording a second solar spectral power distribution from the common sampling structure when the switch is in the second operative position. Finally, comparing the first solar spectral power distribution to the second solar spectral power distribution to determine a concentration factor of the outdoor accelerated weathering device.

In another aspect of the present disclosure, a method for calibrating a spectral measuring assembly mounted on an outdoor weathering device exposed to direct sunlight includes a number of steps. Namely, orienting the spectral measuring assembly on the outdoor weathering device for exposure to direct sunlight wherein the spectral measuring assembly includes a first light collection device and a first sampling structure and whereby the direct sunlight is channeled from the first light collection device to the first sampling structure. Next, orienting a standards-traceable spectral measuring assembly on a support adjacent the at least one outdoor weathering device for exposure to direct sunlight, the standards-traceable spectral measuring assembly including a second light collection device and a second sampling structure, whereby the direct sunlight is channeled from the second light collection device to the second sampling structure and wherein the first and second light collection devices are substantially identical and the first and second sampling structures are substantially identical. Next, triggering simultaneous recordation of a solar spectral power distribution from each spectral measuring assembly (on the outdoor weathering device) and the standards-traceable spectral measuring assembly (adjacent to the outdoor weathering device). Finally, comparing the solar spectral power distribution from each spectral measuring assembly to the solar spectral power distribution form the standards-traceable spectral measuring assembly to determine a standards-traceable calibration factor for the spectral measuring assembly (mounted on the outdoor weathering device).

In another aspect the present disclosure, a method for determining an offset factor for one outdoor accelerated weathering device of a plurality of outdoor accelerated weathering devices with respect to each of other of the plurality of outdoor accelerated weathering devices includes a number of steps. Namely, orienting a first spectral measuring assembly on each of the plurality of outdoor accelerated weathering devices, wherein each first spectral measuring assembly includes a first light collection device disposed on a target board of the accelerated weathering device for exposure to concentrated sunlight and first sampling structure, wherein the concentrated sunlight is channeled to the first sampling structure. Next, recording a solar spectral power distribution of the concentrated sunlight channeled to the first sampling structure for each of the plurality of outdoor accelerated weathering devices. Finally, comparing the solar spectral power distribution from the one outdoor accelerated weathering device to the solar spectral power distribution from the other of the plurality of outdoor accelerated weathering devices to determine to the offset factor for the one outdoor accelerated weathering device with respect to the other of the plurality of outdoor accelerated weathering devices.

In another aspect of the present disclosure, a method for determining a correlation factor for each of a direct sunlight weathering device, an outdoor accelerated weathering device and an indoor accelerated weathering device with respect to one another includes a number of steps and substeps. Namely, mounting: (i) a first test specimen on the direct sunlight weathering device; (ii) a second test specimen on the outdoor accelerated weathering device; and (iii) a third test specimen on the indoor accelerated weathering device, wherein the first, second and third test specimens are substantial identical, Next, positioning: (i) a first spectral measuring assembly adjacent the first test specimen; (ii) a second spectral measuring assembly adjacent the second test specimen; and (iii) a third spectral measuring assembly adjacent the third test specimen, wherein the first, second and third spectral measuring assemblies are substantial identical. Next, exposing: (i) the first test specimen and the first spectral measuring assembly to direct sunlight for a first desired measure; (ii) the second test specimen and the second spectral measuring assembly to concentrated sunlight for a second desired measure; and (iii) the third test specimen and the third spectral measuring assembly to artificial light for a third desired measure, wherein the first, second and third measures are substantially identical. Next, monitoring: (i) the first test specimen over the first desired measure at a predetermined wavelength interval; (ii) the second test specimen over the second desired measure at the predetermined wavelength interval; and (iii) the third test specimen over the third desired measure at the predetermined wavelength interval. Next, determining material property changes as a function of spectral light exposure in the first, second, and third test specimens periodically. Next, recording each of the determined material property changes in the first, second and third test specimens. Next, comparing the determined material property changes of the first and second test specimens to determine an outdoor-accelerated correlation factor. Next, comparing the determined material property changes of the first and third test specimens to determine an outdoor-indoor correlation factor. Finally, comparing the determined material property changes of the second and third specimens to determine an accelerated-indoor correlation factor.

In another aspect of the present invention, a method for determining a correlation factor between an outdoor accelerated weathering device and indoor accelerated weathering device includes a number of steps. Namely, mounting: (i) a first test specimen on the outdoor accelerated weathering device, and (ii) a second test specimen on the indoor accelerated weathering device, wherein the first and second test specimens are substantially identical. Next, positioning: (i) a first spectral measuring assembly adjacent the first test specimen; and (ii) a second spectral measuring assembly adjacent the second test specimen, wherein the first and second spectral measuring assemblies are substantially identical. Next, exposing: (i) the first test specimen and first spectral measuring assembly to concentrated sunlight for a first desired measure; and (ii) the second test specimen and second spectral measuring assembly to artificial light for a second desired measure, wherein the first and second measures are substantially identical. Next, monitoring: (i) the first test specimen over the first desired measure at a predetermined wavelength interval; and (ii) the second test specimen over the second desired measure at the predetermined wavelength interval. Next, determining material property changes as a function of spectral light exposure in the first and second test specimens periodically. Next, recording each of the determined material property changes in the first and second test specimens. Finally, comparing the determined material property changes of the first and second test specimens to determine and accelerated-indoor correlation factor.

In another aspect of the present disclosure, a method of accelerated weathering a test specimen disposed in an indoor accelerated weathering device includes exposing the test specimen to an artificial light source for a predetermined measure based on an accelerated-indoor correlation factor.

In another aspect of the present disclosure, a method for determining a correlation factor between a direct sunlight weathering device and an indoor accelerated weathering device includes a number of steps. Namely, mounting (i) a first test specimen on the direct sunlight weathering device; and (ii) a second test specimen on the indoor accelerated weathering device, wherein, the first and second test specimens are substantially identical. Next, positioning (i) a first spectral measuring assembly adjacent to the first test specimen; and (ii) a second spectral measuring assembly edges the second test specimen, wherein the first and second spectral measuring assemblies are substantially identical. Next, exposing (i) the first test specimen and the first spectral measuring assembly to direct sunlight for a first desired measure; and (ii) the second test specimen and the second spectral measuring assembly to artificial light for a second desired measure; wherein the first and second measures are substantially identical. Next, monitoring (i) the first test specimen over the first desired measure at a predetermined wavelength interval; and (ii) the second test specimen over the second desired measure at the predetermined wavelength interval. Next, determining material property changes as function of spectral light exposure in the first and second test specimens periodically. Next, recording each of the determined material property changes in the first and second test specimens. Finally, comparing the determined material property changes of the first and second test specimens to determine an outdoor-indoor correlation factor.

In another aspect of the present disclosure, a method of accelerated weathering a test specimen disposed in an indoor accelerated weathering device includes exposing the test specimen to an artificial light source for a predetermined measure based on an outdoor-indoor correlation factor.

Figure 1:
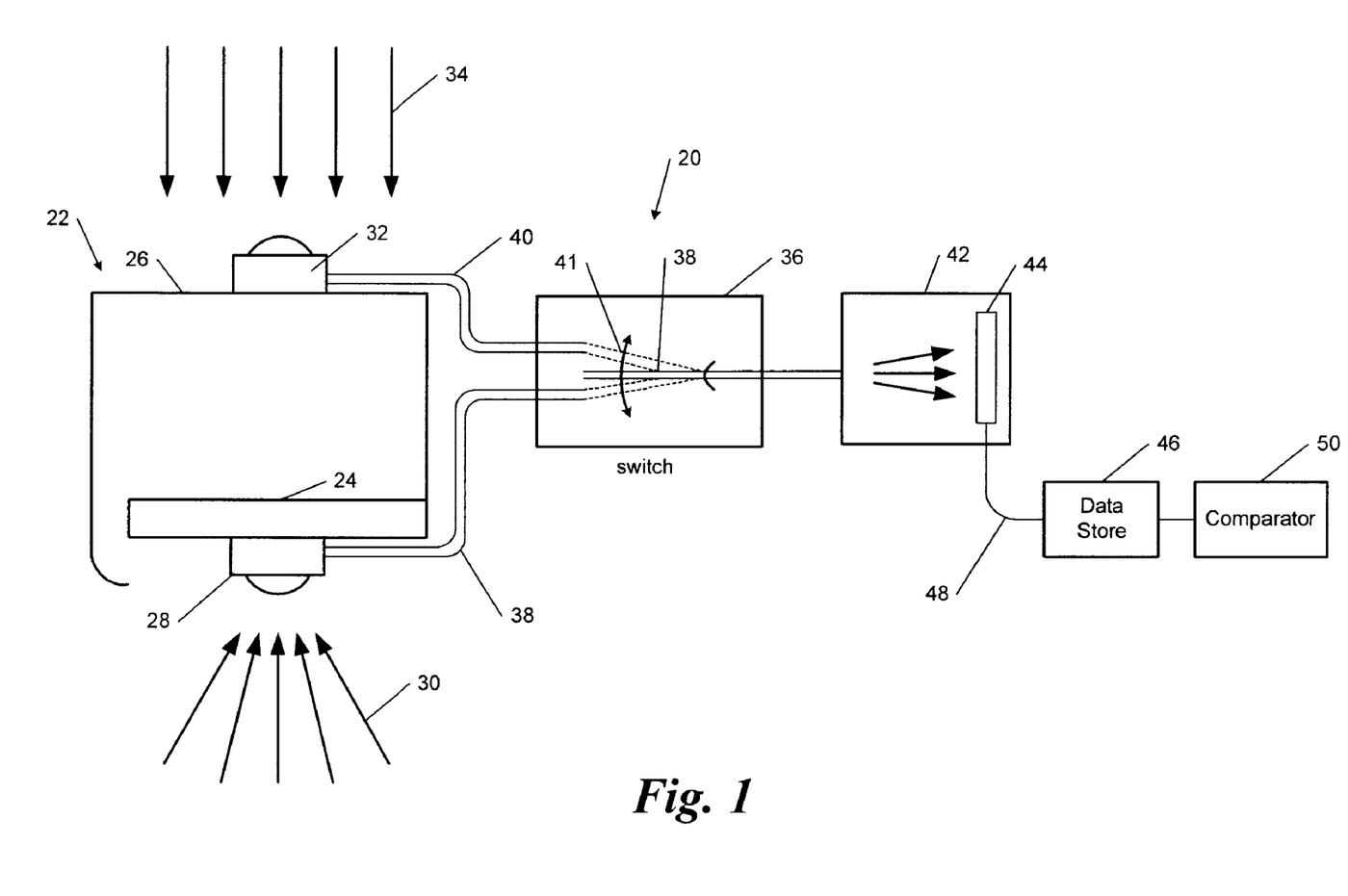
FIG. 1 illustrates a schematic representation of an assembly configured to facilitate performance of a method in accordance with one embodiment of the present disclosure.

FIG. 1 illustrates the schematic representation of an assembly 20 configured to facilitate performance of a method in accordance with one embodiment of the present disclosure. The assembly 20 is useful in connection with a method for determining a concentration factor of an outdoor accelerated weathering device. An air tunnel 22 of an outdoor accelerated weathering device is shown in detail without the remainder of the outdoor accelerated weathering device for clarity. It will be recognized by those of ordinary skill in the art that the air tunnel 22 is merely a component of a conventional outdoor accelerated weathering test apparatus, such as made be described in U.S. Pat. Nos. 6,533,452, 6,659,638 and/or 6,990,868, commonly owned by the assignee hereof and each incorporated by reference herein. The air tunnel 22 includes a target board 24 and an upper surface 26.

In this embodiment of the present disclosure, a first light collection device 28 is oriented on the target board 24 for exposure to concentrated sunlight 30. A second light collection device 32 is oriented on the upper surface 26 for exposure to direct sunlight 34. The first and second light collection devices 28, 32 are substantially identical. As used in this disclosure, the term light collection devices shall be construed broadly and not in a limiting sense to include, among others suitable devices, any front end optics, diffuser, lenses, fiber-optics, fiber optic cables, fiber optic bundles, mirrors, quartz light tube or any other suitable device.

The concentrated sunlight 30 from the first light collection device 28 is channeled to a switch 36 by a guide 38. The direct sunlight 34 from the second light collection device 32 is channeled to the switch 36 by another guide 40. It will be recognized by those of skill in the art that use of the term guide shall not be construed in a limiting sense rather the step of channeling may be provided in accordance with any suitable device including without limitation, any device capable of transmitting light or electrical signals or any other suitable device. Additionally, the switch 36 shall be construed without limitation such that the function of the switch 36 is to select to channel the concentrated sunlight or direct sunlight, or any electrical or other optical signal associated and representative thereof. Further, the switch 36 includes an element 38 which facilitates selection of channeling the concentrated sunlight or the direct sunlight. Such that the switch 36 may be actuated between a first operative position and a second operative position by directing in accordance with arrow 41. It will be recognized by those of skill in the art that the first operative position may be to link the concentrated sunlight to a spectrum measuring device or to link the direct sunlight to the spectral measuring device. Likewise, the second operative position may be to link the concentrated sunlight to the spectral measuring device or may be to link the direct sunlight to the spectral measuring device.

Actuating the switch between the first operative position and the second operative position will result in one of the concentrated sunlight 30 from the first light collection device 28 and the direct sunlight 34 from the second light collection device 32 to be directed to a common sampling structure 42 in the first operative position and an other of the concentrated sunlight 30 from the first light collection device 28 and the direct sunlight 34 from the second light collection device 32 to be directed to the common sampling structure 42 in the second operative position. It is within the teachings of the present disclosure that the common sampling structure is to be construed without limitation and may include a suitable device, for example, integrating sphere, observation wall, prism or any other suitable device.

A spectral measuring device 44 is oriented to observe the concentrated sunlight 30 and the direct sunlight 34 on the common sampling structure 42 as the switch 36 is actuated between the first and second operative positions. It is also within the teachings of the present disclosure that the spectral measuring device is to be construed without limitation as any suitable device to perform the function, such as, for example, a charged couple device or any other suitable device.

A data store 46 records a first solar spectral power distribution from the common sampling structure 42 when the switch is in the first operative position and records a second solar spectral power distribution from a common sampling structure 42 when the switch is in the second operative position. The data store 46 is connected by cable 48 to the common sampling structure 42 to facilitate such recordation. As within the teachings of the present invention that the term cable is to be construed without limitation as device or method suitable to fulfill the function of delivering a signal, such as, for example, any wired or wireless connection or any other suitable device. Additionally, the term data store is to be construed without limitation as any suitable device, method or capability to perform the intended function, such as, for example, a computer, personal digital assistant phone, RAM, ROM, spreadsheet, software, or any other suitable application.

A comparator 50 compares the first solar spectral power distribution to the second solar spectral power distribution to determine a concentration factor of the outdoor accelerated weathering device. The first and second solar spectral power distributions each include a predetermined wavelength interval and an amplitude associated with each respective wavelength within the predetermined wavelength interval. Accordingly, the concentration factor includes a predetermined wavelength interval and amplitude associated with each respective wavelength within the predetermined wavelength interval representing a difference between the amplitude for the first solar spectral power distribution and amplitude for the second solar spectral power distribution for each respective wave length within the predetermined wavelength interval. It is within the teachings of the present disclosure that the comparator be construed without limitation to include any suitable device capable of performing the intended function such as, for example, a computer, a personal digital assistant, phone, communication device or any other suitable hardware or software application therefore. After determining the concentration factor, a measure for exposure of a test specimen may be determined based on the first solar spectral power distribution and the concentration factor for a predetermined wavelength interval. Accordingly, as a result, a precise dosage may be determined for the test specimen.

Figure 2:
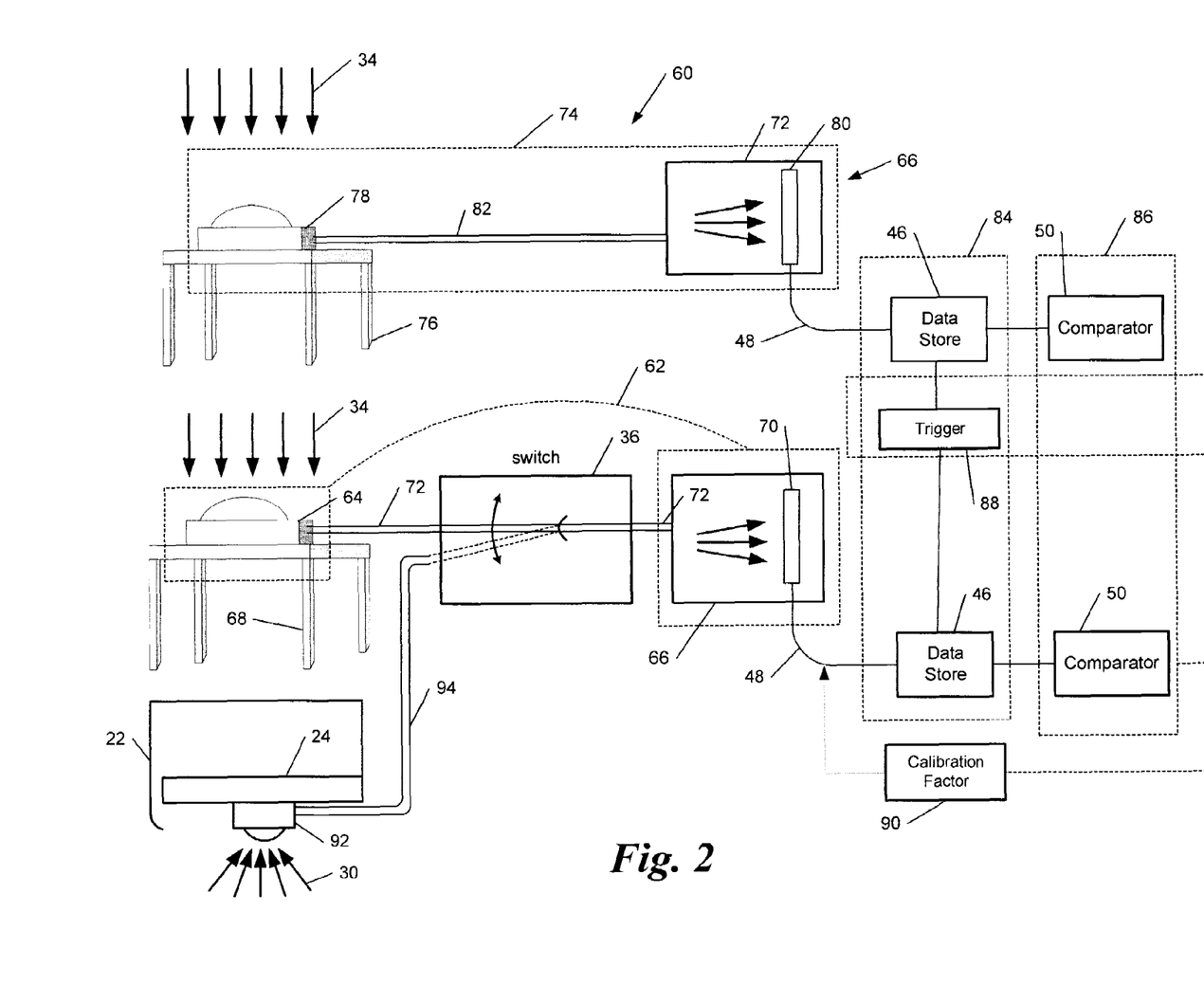
FIG. 2 illustrates a schematic representation of an assembly configured to facilitate performance of a method in accordance with one embodiment of the present disclosure.

FIG. 2 illustrates a schematic representation of an assembly 60 that facilitates performance of a method in accordance with the present disclosure. In this embodiment, the assembly 60 facilitates performing a method for calibrating a spectral measuring assembly mounted on an outdoor weathering device exposed to direct sunlight. A spectral measuring assembly 62 includes a first light collection device 64 and a first sampling structure 66. It will be recognized by those of skill in the art that the term spectral measuring assembly shall be construed without limitation as any assembly of devices suitable to perform the intended function as described above in more detail, mainly at least a light collection device, guide, spectral measuring device and sampling structure and any other suitable device. Here and after, the term spectral measuring assembly shall be construed accordingly without need to resort to the details of individual construction. The spectral measuring assembly is oriented on an outdoor weathering device 68 for exposure to direct sunlight 34. In this embodiment, the outdoor weathering device may be a simple rack or any other suitable device for exposing the spectral measuring assembly 62 to direct sunlight. The direct sunlight 34 is channeled from the first light collection device 64 to the first sampling structure 70 by way of guide 72.

A standard-traceable spectral measuring assembly 74 is oriented on a support 76 adjacent to the outdoor weathering device 68 for exposure to direct sunlight 34. The standards-traceable spectral measuring assembly 74 includes a second light collection device 78 and a second sampling structure 80, whereby the direct sunlight 34 is channeled from the second light collection device 78 to the second sampling structure 80 via guide 82. The first and second light collection devices 64, 78 are substantially identical and the first and second sampling structures 70, 80 are substantially identical. A data store 46 and comparator 50 are connected to each of the spectral measuring assembly 62 and standards-traceable spectral measuring assembly 74 via a link 48 which carries a signal from the sampling structure 70 or 80 to the respective data store 46. It is within the teachings of the present invention that the data store 46 may be configured as a single device 84. Likewise, the comparators 50 may also be configured as a signal device 86. It is still further within the teachings of the present disclosure that the data store 46 may in fact be a subset, subcomponent or subassembly of the comparator 50.

A solar spectral power distribution from each of the spectral measuring assembly 62 and the standards traceable spectral measuring assembly 74 are simultaneously recorded in the data store 46 upon actuation of the trigger 88 that is linked to each respective data store 46. The solar spectral power distribution from the spectral measuring assembly 62 is compared to the solar spectral power distribution from the standards-traceable spectral measuring assembly 74 to determine a standards-traceable calibration factor 90 for the spectral measuring assembly 62. In a feedback mode, the standards-traceable calibration 90 may be applied to an output from the spectral measuring device 62 via link 48. Preferably, the steps of actuating the trigger 88, comparing the solar spectral power distribution of the spectral measuring assembly 62 and the standards-traceable spectral measuring assembly 74 and applying the standards-traceable calibration factor to an output from the spectral measuring assembly 62 are periodically repeated with a desired frequency.

In another embodiment of the present disclosure, a standards-traceable concentration factor, for the outdoor accelerated weathering device may be determined. A third light collection device 92 may be oriented on a target board 24 of the outdoor accelerated weathering device for exposure to concentrated sunlight 30. The first and third light collection devices 64, 92 are substantially identical. A switch 36 may be oriented between the first and second light collection devices 64, 92 and the first sampling structure 70. The concentrated sunlight 30 is channeled to the first sampling structure 70 via guide 94.

In a similar manner as described above, actuating the switch 36 between a first operative position and a second operative position such that one of the direct sunlight 34 from the first light collection via 64 and the concentrated sunlight 30 from the third light collection device 92 is directed to the first sampling structure 70 in the first operative position and an other of the direct sunlight 34 from the first light collection device 64 and the concentrated sunlight 30 from the third light collection device 92 is directed to the first sampling structure 70 in the second operative position. As additionally generally described above, the trigger 88 may be then actuated to simultaneously record the solar spectral power distribution from the third light collection device 92 and the first sampling structure 70 and from the standards-traceable spectral measuring assembly 74 when the switch is in the first operative position. Then, the solar spectral power distribution from the third light collection device 92 and the first sampling structure 70 and from the standards-traceable spectral measuring assembly 74 may be compared to determine a standards-traceable concentration factor for the outdoor accelerated weathering device.

Each solar spectral power distribution includes a predetermined wavelength interval and an amplitude associated with each respective wavelength within the predetermined wavelength interval. Moreover, the standards-traceable concentration factor includes a predetermined wavelength interval and an amplitude associated with each respective wavelength within the predetermined wavelength interval representing a difference between the amplitude for the solar spectral power distribution from the third light collection device 92 and the first sampling structure 70 and the amplitude for the solar spectral power distribution from the standards-traceable spectral measuring assembly 74 for each respective wavelength within the predetermined wavelength interval. As a result, a measure for exposure of a test specimen mounted on a target board of the outdoor accelerated weathering device may be determined based on the solar spectral power distribution from the third light collection device 92 and the first sampling structure 70 and the concentration factor for a predetermined wavelength interval.

Figure 3:
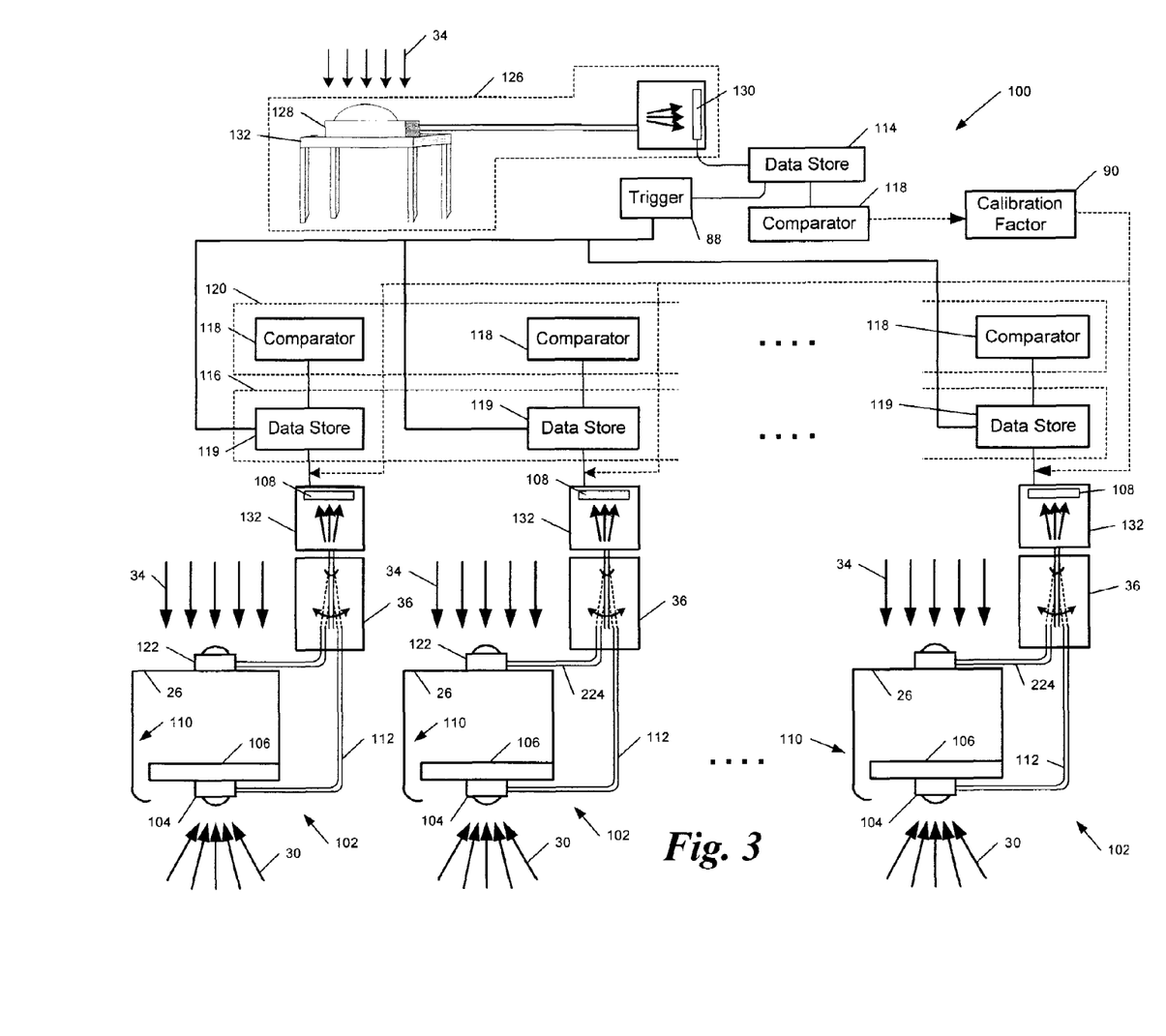
FIG. 3 illustrates a schematic representation of an assembly configured to facilitate performance of a method in accordance with one embodiment of the present disclosure.

FIG. 3 illustrates a schematic representation of an assembly 100 that facilitates performance of a method in accordance with one embodiment of the present disclosure. The assembly 100 enables performance of a method for determining an offset factor for one outdoor accelerated weathering device of a plurality of outdoor accelerated weathering devices with respect to each other of the plurality of outdoor accelerated weathering devices. A first spectral measuring assembly 102 (including a first light collection device 104 disposed on a target board 106 of the accelerated weathering device for exposure to concentrated sunlight 30 and a first sampling structure 108) on each of the plurality of outdoor accelerated weathering devices 110. The concentrated sunlight 30 is channeled to the first sampling structure 108 via guide 112 which may pass through switch 36.

A solar spectral power distribution of the concentrated sunlight 30 channeled to the first sampling structure 108 is recorded in a data store 119 linked to the first sampling structure 108 for each of the plurality of outdoor accelerated weathering devices. The solar spectral power distribution from one of the outdoor accelerated weathering devices is compared to the solar spectral power distribution from the other of the plurality of outdoor accelerated weathering devices to determine the offset factor for the one outdoor accelerated weathering device with respect to the other of the plurality of outdoor accelerated weathering devices. As mentioned above, the data store associated with each outdoor accelerated weathering device may be individually associated therewith or a common data store 116 may be provided. Likewise an individual comparator 118 may be associated with each individual outdoor accelerated weathering device or a common comparator 120 may be associated with the plurality of outdoor accelerated weathering devices.

The solar spectral power distribution for each spectral measuring assembly 102 includes a predetermined wavelength interval and an amplitude associated with each respective wavelength within the predetermined wavelength interval.

Preferably, the steps of recording the solar spectral power distribution for each outdoor accelerated weathering device and comparison of same to the solar spectral power distribution for each of the other of the plurality of outdoor accelerated weathering devices is periodically repeated at a desirable frequency. As a result, change, in each outdoor accelerated weathering device with respect to anyone of the other of the plurality of outdoor accelerated weathering devices may be easily detected. Monitoring for such a change in the offset for one outdoor accelerated weathering device may be useful to determine if maintenance for such device is necessary.

The method described in this embodiment is also useful for adjusting a duration of exposure for a test specimen mounted on the one accelerated weathering test device based on a desired solar radiant exposure, the solar spectral power distribution for the one of the plurality of accelerated weathering devices and the offset for the one of the plurality of accelerated weathering devices at a predetermined wavelength interval. Moreover, the method in this embodiment of the present disclosure is useful in determining a solar radiant exposure for a test specimen mounted on the one accelerated weathering device based on a desired duration of exposure for the one of the plurality of outdoor accelerated weathering devices, a desired solar power spectral power distribution for the one of the plurality of outdoor accelerated weathering devices and the offset for the one of the plurality of outdoor accelerated weathering devices at a predetermined wavelength interval.

In another embodiment of the present disclosure, the method further includes orienting a second light collection device 122 on an upper surface 26 of each of the plurality of outdoor accelerated weathering devices for exposure to direct sunlight 34 so that the direct sunlight 34 may be channeled to the first sampling structure 108 via guide 224.

A switch 36 may be oriented between the first sampling structure 108 and the first and second light collection devices 104, 122, such that the switch 36 may be actuated between the first operative position, where one of the concentrated sunlight 30 from the first light collection device 104 and the direct sunlight 34 from the second light collection device 122 is directed to the first sampling structure 108, and a second operative position, where an other of the concentrated sunlight 30 from the first light collection device 104 and the direct sunlight 34 from the second light collection device 122 is directed to the first sampling structure 108 in the second operative position.

A standards-traceable spectral measuring assembly 126 including a third light collection device 128 and a second sampling structure 130 are disposed on a support 132 adjacent to the plurality of outdoor accelerated weathering devices 110 for exposure to direct sunlight 34. Each of the first, second and third light collection devices 104, 122, 128 are substantially identical and each of the first and second sampling structures 108, 130 are also substantially identical.

As generally described above, a data store 114 and comparator 118 are linked to the standards-traceable spectral measuring assembly 126. A trigger 88 is useful to actuate simultaneous recordation of the solar spectral power distribution from each first sampling structure 108 when the switch is actuated to the second operative position and the standards-traceable spectral measuring assembly 126. The solar spectral power distribution from each first sampling structure 108 when the switch is in the second operative position and the standards-traceable spectral measuring assembly 126 may be then compared to determine a standards-traceable calibration factor 90 for the second light collection device 122 and first sampling structure 108 combination on each of the plurality of outdoor weathering devices. In a feedback mode, the standards-traceable calibration factor 90 may be applied to an output from the first spectral measuring assembly 102. Preferably, the triggering, comparing and applying steps are periodically repeated at a desired frequency.

In another embodiment of the present disclosure, the method may further include determining a standards-traceable concentration factor for each of the outdoor accelerated weathering devices. For each of the outdoor accelerated weathering devices, the switch is actuated to the first operative position and the trigger 88 is actuated to simultaneously record the solar spectral power distribution from the first sampling structure 108 and the standard-traceable spectral measuring assembly 126. The solar spectral power distribution from the first sampling structure 108 when the switch is in the first operative position is then compared to the solar spectral power distribution from the standards-traceable spectral measuring assembly 126 to determine the concentration factor for each of the plurality of outdoor accelerated weathering devices.

Figure 4:
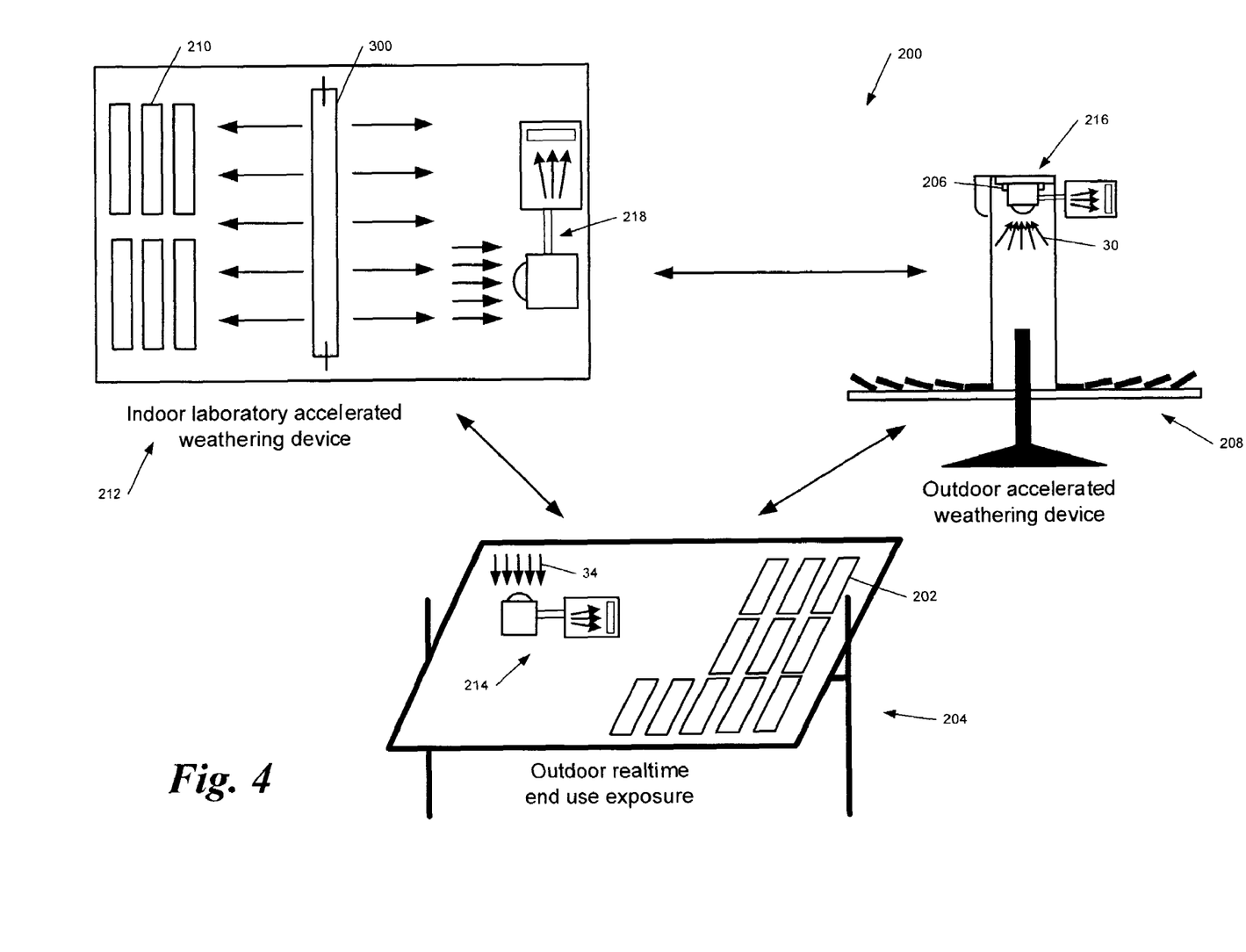
FIG. 4. illustrates a schematic representation of an assembly configured to facilitate performance of a method in accordance with one embodiment of the present disclosure.
Figure 5:
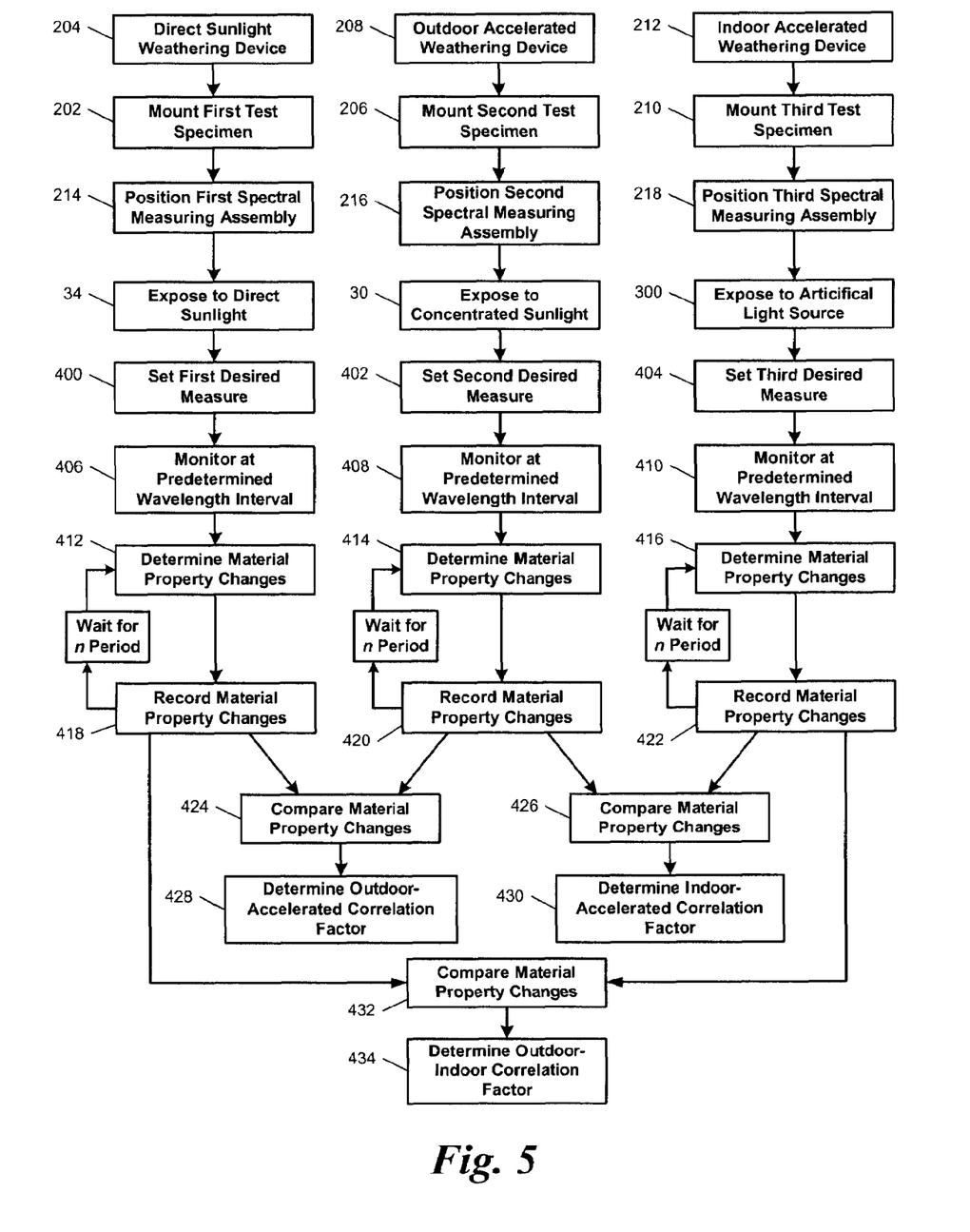
FIG. 5 illustrates a schematic representation of an assembly configured to facilitate performance of a method in accordance with one embodiment of the present disclosure.

FIG. 4 illustrates a schematic representation of an assembly useful to facilitate a method in accordance with one embodiment of the present disclosure. The assembly 200 is useful in connection with a method for determining the correlation factor for each of a direct sunlight weathering device 204, an outdoor accelerated weathering device 208 and an indoor accelerated weathering device 212 with respect to one another, as also illustrated in FIG. 5. A first test specimen 202 is mounted on the direct sunlight weathering device 204. A second test specimen 206 is mounted on the outdoor accelerated weathering device 208. A third test specimen 210 is mounted on the indoor accelerated weathering device 212. The first, second and third test specimens 202, 206, 210 are preferably substantially identical.

A first spectral measuring assembly 214 is positioned adjacent the first test specimen 202. A second spectral measuring assembly 216 is positioned adjacent the second test specimen 206. A third spectral measuring assembly 218 is positioned adjacent the third test specimen 210. The first, second and third spectral measuring assemblies 214, 216, 218 are preferably substantially identical. The first test specimen 202 and the first spectral measuring assembly 214 are exposed to direct sunlight 34 for a first desired measure. The second test specimen 206 and the second spectral measuring assembly 216 are exposed to concentrated sunlight 30 for a second desired measure. The third test specimen 210 and a third spectral measuring assembly 218 are exposed to an artificial light source 300 for a third desired measure. The first, second and third measures (in steps 400, 402 and 404, respectively, in FIG. 5) are preferable set to be substantially identical and will be recognized by those of skill in the art to be a preselected period of time.

The first test specimen 202 is monitored over the first desired measure at a predetermined wavelength interval in step 406 of FIG. 5. The second test specimen 206 is monitored over the second desired measure at the predetermined wavelength interval in step 408 of FIG. 5. The third test specimen 210 is monitored over the third desired measure at the predetermined wavelength interval in step 410 of FIG. 5. It will be recognized by those of skill in the art that the predetermined wavelength interval may be any such interval suitable for the test specimens based on any suitable or desirable control parameter. For example, the predetermined wavelength interval may be a single identifiable wavelength, a range of wavelengths or any other suitable identification of wavelength as additionally discussed above.

Material property changes as a function of spectral light exposure in each of the first, second and third test specimens 202, 206, 210 are determined in respective steps 412, 414, 416 of FIG. 5. One of skill in the art will recognize that such determination may be made in any preferable or suitable manner with respect to the composition or desired outcome of the test specimens. Each of the determined material property changes in the first, second and third test specimens 202, 206, 210 is then recorded in respective steps 418, 420, 422 of FIG. 5. On a periodic basis, after waiting for a preselected period of time or for an "n" period, which may be an increment of time, light dose, radiant exposure or other suitable measurement, steps 412, 414, 416 and 418, 420, 422 are continuously repeated for the respective first, second and third desired measures, wherein the "n" period is any desired increment of time desirable or suitable for monitoring the material property changes as a function of spectral light exposure in view of the test specimens.

After the expiration of the first, second and third desired measures, an outdoor-accelerated correlation factor may be determined in step 428 of FIG. 5 by comparing the material property changes of the first and second test specimens 202, 206 as a function of the spectral light exposure in step 424 of FIG. 5. An outdoor-indoor correlation factor may be determined in step 430 of FIG. 5 by comparing the material property changes of the first and third test specimens 202, 210 in step 426 of FIG. 5. An accelerated-indoor correlation factor may be determined in step 432 of FIG. 5 by comparing the material property changes of the second and third test specimens 206, 210 in step 434 of FIG. 5. It will be recognized by those of skill in the art that any combination of weathering devices may be compared to determine the correlation factor therebetween and that the comparison of such material property changes may be in accordance with any suitable or desirable factor, parameter or composition.

For example, methods may be performed in a similar manner for determining a correlation factor between an outdoor accelerated weathering device and an indoor accelerated weathering device, between a direct sunlight weathering device and an indoor accelerated weathering device and between a direct sunlight weathering device and an outdoor accelerated weathering device. As a result of determining an accelerated-indoor correlation factor, a method of accelerated weathering a test specimen disposed in an indoor accelerated weathering device comprises exposing the test specimen to an artificial light source for a predetermined measure based on the accelerated-indoor correlation factor. Likewise, as a result of determining an outdoor-indoor correlation factor, a method of accelerated weathering a test specimen disposed in an indoor accelerated weathering device includes exposing the test specimen to an artificial light source for a predetermined measure based on the outdoor-indoor correlation factor. Still further, as a result of determining an outdoor-accelerated correlation factor, a method of accelerated weathering a test specimen disposed on an outdoor accelerated weathering device includes exposing the test specimen to concentrated sunlight for a predetermined measure based on the outdoor-accelerated correlation factor.

Furthermore, while the particular preferred embodiments have been shown and described, it will be obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

What is claimed is:

1. A method for determining a concentration factor for an outdoor accelerated weathering device, the method comprising:

orienting a first light collection device on a target board of the outdoor accelerated weathering device for exposure to concentrated sunlight;

orienting a second light collection device on an upper surface of the outdoor accelerated weathering device for exposure to direct sunlight, wherein the first and second light collection devices are substantially identical;

channeling the concentrated sunlight from the first light collection device and the direct sunlight from the second light collection device to a switch;

actuating the switch between a first operative position and a second operative position such that one of the concentrated sunlight from the first light collection device and the direct sunlight from the second light collection device is directed to a common sampling structure in the first operative position and an other of the concentrated sunlight from the first light collection device and the direct sunlight from the second light collection device is directed to the common sampling structure in the second operative position;

orienting a spectral measuring device to observe the concentrated sunlight and direct sunlight on the common sampling structure as the switch is actuated between the first and second operative positions;

recording a first solar spectral power distribution ("SSPD") from the common sampling structure when the switch is in the first operative position;

recording a second SSPD from the common sampling structure when the switch is in the second operative position;

comparing the first SSPD to the second SSPD to determine a concentration factor of the outdoor accelerated weathering device.

2. The method of claim 1, wherein the first and second SSPD each include a predetermined wavelength interval and an amplitude associated with each respective wavelength within the predetermined wavelength interval.

3. The method of claim 1, wherein the concentration factor includes a predetermined wavelength interval and an amplitude associated with each respective wavelength within the predetermined wavelength interval representing a difference between the amplitude for the first SSPD and the amplitude for the second SSPD for each respective wavelength within the predetermined wavelength interval.

4. The method of claim 1, further comprising determining a measure for exposure of a test specimen based on the first SSPD and the concentration factor for a predetermined wavelength interval.

5. A method for calibrating a spectral measuring assembly mounted on an outdoor weathering device exposed to direct sunlight, the method comprising:
orienting the spectral measuring assembly on the outdoor weathering device for exposure to direct sunlight, the spectral measuring assembly including a first light collection device and a first sampling structure, whereby the direct sunlight is channeled from the first light collection device to the first sampling structure;
orienting a standards-traceable spectral measuring assembly on a support adjacent to the outdoor weathering device for exposure to direct sunlight, the standards-traceable spectral measuring assembly including a second light collection device and a second sampling structure, whereby the direct sunlight is channeled from the second light collection device to the second sampling structure, wherein the first and second light collection devices are substantially identical and the first and second sampling structures are substantially identical;
triggering simultaneous recordation of a solar spectral power distribution ("SSPD") from the spectral measuring assembly and the standards-traceable spectral measuring assembly;
comparing the SSPD from the spectral measuring assembly to the SSPD from the standards-traceable spectral measuring assembly to determine a standards-traceable calibration factor for the spectral measuring assembly.

6. The method of claim 5, further comprising applying the standards-traceable calibration factor to an output from the spectral measuring device.

7. The method of claim 6, further comprising repeating periodically the triggering step, the comparing step and the applying step.

8. The method of claim 5, further comprising determining a standards-traceable concentration factor for the outdoor accelerated weathering device, the method comprising:
orienting a third light collection device on a target board of the outdoor accelerated weathering device for exposure to concentrated sunlight, wherein the first and third light collection devices are substantially identical;
channeling the concentrated sunlight to the first sampling structure;
orienting a switch between the first and second light collection devices and the first sampling structure;
actuating the switch between a first operative position and a second operative position such that one of the direct sunlight from the first light collection device and the concentrated sunlight from the third light collection device is directed to the first sampling structure in the first operative position and an other of the direct sunlight from the first light collection and the concentrated sunlight from the third light collection device is directed to the first sampling structure in the second operative position;
triggering simultaneous recordation of the SSPD from the third light collection device and the first sampling structure and from the standards-traceable spectral measuring assembly when the switch is in the first operative position;
comparing the SSPD from the third light collection device and the first sampling structure and from the standards-traceable spectral measuring assembly to determine a standards-traceable concentration factor for the outdoor accelerated weathering device.

9. The method of claim 8, wherein each SSPD includes a predetermined wavelength interval and an amplitude associated with each respective wavelength within the predetermined wavelength interval.

10. The method of claim 8, wherein the standards-traceable concentration factor includes a predetermined wavelength interval and an amplitude associated with each respective wavelength within the predetermined wavelength interval representing a difference between the amplitude for the SSPD from the third light collection device and the first sampling structure and the amplitude for the SSPD from the standards-traceable spectral measuring assembly for each respective wavelength within the predetermined wavelength interval.

11. The method of claim 9, further comprising determining a measure for exposure of a test specimen based on the SSPD from the third light collection device and the first sampling structure and the concentration factor for a predetermined wavelength interval.

12. A method for determining an offset factor for one outdoor accelerated weathering device of a plurality of outdoor accelerated weathering devices with respect to each other of the plurality of outdoor accelerated weathering devices, the method comprising:
orienting a first spectral measuring assembly on each of the plurality of outdoor accelerated weathering devices, wherein each first spectral measuring assembly includes a first light collection device disposed on a target board of the accelerated weathering device for exposure to concentrated sunlight and a first sampling structure, wherein the concentrated sunlight is channeled to the first sampling structure;
recording a solar spectral power distribution ("SSPD") of the concentrated sunlight channeled to the first sampling structure for each of the plurality of outdoor accelerated weathering devices;
comparing the SSPD from the one outdoor accelerated weathering device to the SSPD from the other of the plurality of outdoor accelerated weathering devices to determine the offset factor for the one outdoor accelerated weathering device with respect to the other of the plurality of outdoor accelerated weathering devices.

13. The method of claim 12, wherein the SSPD for each spectral measuring device includes a predetermined wavelength interval and an amplitude associated with each respective wavelength within the predetermined wavelength interval.

14. The method of claim 12, further comprising repeating periodically the recording and comparing steps.

15. The method of claim 12, further comprising adjusting a duration of exposure for a test specimen mounted on the one outdoor accelerated weathering device based on a desired solar radiant exposure, the SSPD for the one of the plurality of outdoor accelerated weathering devices and the offset for the one of the plurality of outdoor accelerated weathering devices at a predetermined wavelength interval.

16. The method of claim 12, further comprising determining a solar radiant exposure for a test specimen mounted on the one outdoor accelerated weathering device based on a desired duration of exposure for the one of the plurality of outdoor accelerated weathering devices, the SSPD for the one of the plurality of outdoor accelerated weathering devices and the offset for the one of the plurality of outdoor accelerated weathering devices at a predetermined wavelength interval.

17. The method of claim 12, further comprising monitoring a change in the offset for the one outdoor accelerated weathering device to determine if maintenance is necessary.

18. The method of claim 12, further comprising:
orienting a second light collection device on an upper surface of each of the plurality of outdoor accelerated weathering devices for exposure to direct sunlight so that the direct sunlight is channeled to the first sampling structure;
orienting a switch between the first sampling structure and the first and second light collection devices, such that the switch may be actuated between a first operative position, where one of the concentrated sunlight from the first light collection device and the direct sunlight from the second light collection device is directed to the first sampling structure, and a second operative position, where an other of the concentrated sunlight from the first light collection and the direct sunlight from the second light collection device is directed to the first sampling structure in the second operative position;
orienting a standards-traceable spectral measuring assembly including a third light collection device and a second sampling structure on a support adjacent the plurality of outdoor accelerated weathering devices for exposure to direct sunlight, wherein each of the first, second and third light collection devices are substantially identical and each of the first and second sampling structures are substantially identical;
triggering simultaneous recordation of the SSPD from each first sampling structure when the switch is actuated to the second operative position and the standards-traceable spectral measuring assembly; and
comparing the SSPD from each first sampling structure when the switch is in the second operative position and the standards-traceable spectral measuring assembly to determine a standards-traceable calibration factor for the second light collection device and first sampling structure combination on each of the plurality of outdoor weathering devices.

19. The method of claim 18, further comprising applying the standards-traceable calibration factor to an output from the first spectral measuring assembly.

20. The method of claim 19, further comprising repeating periodically the triggering step, the comparing step and the applying step.

21. The method of claim 18, further comprising determining a standards-traceable concentration factor for each of the outdoor accelerated weathering devices comprising:
for each of the outdoor accelerated weathering devices, channeling the direct sunlight from the second light collection device and the concentrated sunlight from the first light collection device to a switch;
actuating the switch to the first operative position;
triggering simultaneous recordation of the SSPD from the first sampling structure when the switch is in the first operative position and from the standards-traceable spectral measuring assembly; and
comparing the SSPD from the first sampling structure when the switch is in the first operative position to the SSPD from the standards-traceable spectral measuring assembly to determine a concentration factor for each of the plurality of outdoor accelerated weathering devices.

22. The method of claim 21, wherein each SSPD includes a predetermined wavelength interval and an amplitude associated with each respective wavelength within the predetermined wavelength interval.

23. The method of claim 21, wherein the concentration factor includes a predetermined wavelength interval and an amplitude associated with each respective wavelength within the predetermined wavelength interval representing a difference between the amplitude for the SSPD from the first sampling structure when the switch is in the first operative position and the SSPD from the standards-traceable spectral measuring assembly for each respective wavelength within the predetermined wavelength interval.

24. The method of claim 21, further comprising adjusting a duration of exposure for a test specimen based on a desired solar radiant exposure, the SSPD from the first sampling structure when the switch is in the first operative position and the concentration factor for a predetermined wavelength interval.

25. The method of claim 21, further comprising determining a solar radiant exposure for a test specimen based on a duration of exposure, the SSPD from the first sampling structure when the switch is in the first operative position and the concentration factor for a predetermined wavelength interval.

26. A method for determining a correlation factor for each of a direct sunlight weathering device, an outdoor accelerated weathering device and an indoor accelerated weathering device with respect to one another, the method comprising:
mounting:
(i) a first test specimen on the direct sunlight weathering device;
(ii) a second test specimen on the outdoor accelerated weathering device; and
(iii) a third test specimen on the indoor accelerated weathering device;
wherein the first, second and third test specimens are substantially identical;
positioning:
(i) a first spectral measuring assembly adjacent the first test specimen;
(ii) a second spectral measuring assembly adjacent the second test specimen; and
(iii) a third spectral measuring assembly adjacent the third test specimen;
wherein the first, second and third spectral measuring assemblies are substantially identical;
exposing:
(i) the first test specimen and the first spectral measuring assembly to direct sunlight for a first desired measure;
(ii) the second test specimen and the second spectral measuring assembly to concentrated sunlight for a second desired measure; and
(iii) the third test specimen and the third spectral measuring assembly to artificial light source for a third desired measure;
wherein the first, second and third measures are substantially identical;
monitoring:
(i) the first test specimen over the first desired measure at a predetermined wavelength interval;
(ii) the second test specimen over the second desired measure at the predetermined wavelength interval; and
(iii) the third test specimen over the third desired measure at the predetermined wavelength interval;
determining material property changes as a function of spectral light exposure in the first, second and third test specimens periodically;
recording each of the determined material property changes in the first, second and third test specimens;

comparing the determined material property changes of the first and second test specimens to determine an outdoor-accelerated correlation factor;

comparing the determined material property changes of the first and third test specimens to determine an outdoor-indoor correlation factor; and comparing the determined material property changes of the second and third test specimens to determine an accelerated-indoor correlation factor.

27. The method of claim 26, wherein the step of determining material property changes as a function of spectral light exposure is performed at a predetermined wavelength interval.

28. A method for determining a correlation factor between an outdoor accelerated weathering device and an indoor accelerated weathering device, the method comprising:
   mounting:
      (i) a first test specimen on the outdoor accelerated weathering device; and
      (ii) a second test specimen on the indoor accelerated weathering device;
   wherein the first and second test specimens are substantially identical;
   positioning:
      (i) a first spectral measuring assembly adjacent the first test specimen; and
      (ii) a second spectral measuring assembly adjacent the second test specimen;
   wherein the first and second spectral measuring assemblies are substantially identical;
   exposing:
      (i) the first test specimen and the first spectral measuring assembly to concentrated sunlight for a first desired measure; and
      (ii) the second test specimen and the second spectral measuring assembly to artificial light for a second desired measure;
   wherein the first and second measures are substantially identical;
   monitoring:
      (i) the first test specimen over the first desired measure at a predetermined wavelength interval; and
      (ii) the second test specimen over the second desired measure at the predetermined wavelength interval;
   determining material property changes as a function of spectral light exposure in the first and second test specimens periodically;
   recording each of the determined material property changes in the first and second test specimens;
   comparing the determined material property changes of the first and second test specimens to determine an accelerated-indoor correlation factor.

29. The method of claim 28, wherein the step of determining material property changes as a function of spectral light exposure is performed at a predetermined wavelength interval.

30. A method of accelerated weathering a test specimen disposed in an indoor accelerated weathering device, the method comprising:
   exposing the test specimen to an artificial light source for a predetermined measure based on an accelerated-indoor correlation factor.

31. A method for determining a correlation factor between a direct sunlight weathering device and an indoor accelerated weathering device, the method comprising:
   mounting:
      (i) a first test specimen on the direct sunlight weathering device; and
      (ii) a second test specimen on the indoor accelerated weathering device;
   wherein the first and second test specimens are substantially identical;
   positioning:
      (i) a first spectral measuring assembly adjacent the first test specimen; and
      (ii) a second spectral measuring assembly adjacent the second test specimen;
   wherein the first and second spectral measuring assemblies are substantially identical;
   exposing:
      (i) the first test specimen and the first spectral measuring assembly to direct sunlight for a first desired measure; and
      (ii) the second test specimen and the second spectral measuring assembly to artificial light for a second desired measure;
   wherein the first and second measures are substantially identical;
   monitoring:
      (i) the first test specimen over the first desired measure at a predetermined wavelength interval; and
      (ii) the second test specimen over the second desired measure at the predetermined wavelength interval;
   determining material property changes as a function of spectral light exposure in the first and second test specimens periodically;
   recording each of the determined material property changes in the first and second test specimens;
   comparing the determined material property changes of the first and second test specimens to determine an outdoor-indoor correlation factor.

32. The method of claim 31, wherein the step of determining material property changes as a function of spectral light exposure is performed at a predetermined wavelength interval.

33. A method of accelerated weathering a test specimen disposed in an indoor accelerated weathering device, the method comprising:
   exposing the test specimen to an artificial light source for a predetermined measure based on an outdoor-indoor correlation factor.

34. A method for determining a correlation factor between a direct sunlight weathering device and an outdoor accelerated weathering device, the method comprising:
   mounting:
      (i) a first test specimen on the direct sunlight weathering device; and
      (ii) a second test specimen on the outdoor accelerated weathering device;
   wherein the first and second test specimens are substantially identical;
   positioning:
      (i) a first spectral measuring assembly adjacent the first test specimen; and
      (ii) a second spectral measuring assembly adjacent the second test specimen;
   wherein the first and second spectral measuring assemblies are substantially identical;
   exposing:
      (i) the first test specimen and the first spectral measuring assembly to direct sunlight for a first desired measure; and (ii) the second test specimen and the second spectral measuring assembly to concentrated sunlight for a second desired measure;

wherein the first and second measures are substantially identical;

monitoring:
 (i) the first test specimen over the first desired measure at a predetermined wavelength interval; and
 (ii) the second test specimen over the second desired measure at the predetermined wavelength interval;

determining material property changes as a function of spectral light exposure in the first and second test specimens periodically;

recording each of the determined material property changes in the first and second test specimens;

comparing the determined material property changes of the first and second test specimens to determine an outdoor-accelerated correlation factor.

35. The method of claim 34, wherein the step of determining material property changes as a function of spectral light exposure is performed at a predetermined wavelength interval.

36. A method of accelerated weathering a test specimen disposed in an outdoor accelerated weathering device, the method comprising:

exposing the test specimen to concentrated sunlight for a predetermined measure based on an outdoor-accelerated correlation factor.

* * * * *